US009324169B2

(12) United States Patent
Labbi et al.

(10) Patent No.: US 9,324,169 B2
(45) Date of Patent: Apr. 26, 2016

(54) IDENTIFYING RELATIONSHIPS BETWEEN ENTITIES USING TWO-DIMENSIONAL ARRAY OF SCALAR ELEMENTS, AND A BLOCK MATRIX

(71) Applicant: International Business Machines Corporation, Armonk, NY (US)

(72) Inventors: Abderrahim Labbi, Thalwil (CH); Michail Vlachos, Rueschlikon (CH)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 250 days.

(21) Appl. No.: 14/070,788

(22) Filed: Nov. 4, 2013

(65) Prior Publication Data

US 2014/0146077 A1 May 29, 2014

(30) Foreign Application Priority Data

Nov. 29, 2012 (GB) .................................. 1221497.9

(51) Int. Cl.
*G06T 11/20* (2006.01)
*G06F 19/24* (2011.01)
*G06K 9/62* (2006.01)

(52) U.S. Cl.
CPC .............. *G06T 11/206* (2013.01); *G06F 19/24* (2013.01); *G06K 9/6253* (2013.01)

(58) Field of Classification Search
USPC ................................................ 706/12, 45, 62
See application file for complete search history.

(56) References Cited

PUBLICATIONS

I. S. Dhillon, "Co-Clustering Documents and Words using Bipartite Spectral Graph Partitioning," In Proc. of International Conference on Knowledge Discovery and Data Mining (KDD), pp. 269-274, 2001.
I. S. Dhillon, et al., "Information-theoretic co-Clustering," In Proc. of International Conference on Knowledge Discovery and Data Mining (KDD), pp. 89-98, 2003.
J. A. Hartigan, "Direct Clustering of a Data Matrix," Journal of the American Statistical Association, 67(337): pp. 123-129, 1972.
F. Pan, et al., "CRD: Fast Co-clustering on Large Datasets Utilizing Sampling-Based Matrix Decomposition," Proc. Int. Conf. Data Eng. Apr. 2008, pp. 1-35.

(Continued)

*Primary Examiner* — David Vincent
(74) *Attorney, Agent, or Firm* — Cantor Colburn LLP

(57) ABSTRACT

A computer-implemented method for identifying relationships between entities includes accessing a first data structure being a two-dimensional array of scalar elements ($e$, $e_{ij}$, $e_{kl}^{(i)}$) representable as a matrix, each of the scalar elements capturing a relationship between two entities; reorganizing the first data structure by clustering the scalar elements separately on each dimension of the two-dimensional array, to obtain a second data structure, representable as a K×M block matrix, wherein each block is a reordered sequence of rows and/or columns of the first data structure; compacting the second data structure by: determining two parallel block sequences, which are the most similar according to a given distance measure, the parallel block sequences being either distinct rows or distinct columns of blocks of the second data structure; and reorganizing the second data structure by merging the two determined sequences into a single block sequence.

15 Claims, 5 Drawing Sheets

S32
S10
S20
$c_2$
$c_8$
$r_i$
$r_k$
$c_j$
$c_l$
$d_3, m_3$
$c_7$
S34
S36
$d_1, m_1$
$d_2, m_2$

(56) References Cited

PUBLICATIONS

S. Papadimitriou, et al., "DisCo: Distributed Co-clustering with Map-Reduce, A Case Study Towards Petabyte-Scale End-to-End Mining," ICDM, Eighth IEEE International Conference on Data Mining, Dec. 2008, pp. 1-10.

J. Sun, C. Faloutsos, S. Papadimitriou, and P. S. Yu, "GraphScope: Parameter-free Mining of Large Time-evolving Graphs," In Proc. of KDD, pp. 687-696, 2007.

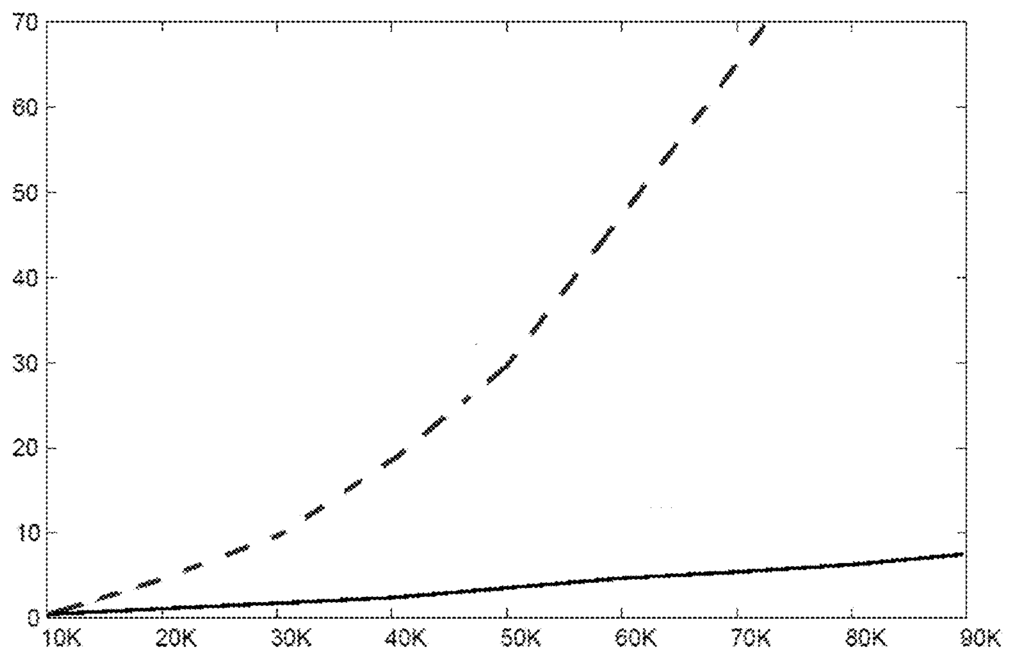
FIG. 9
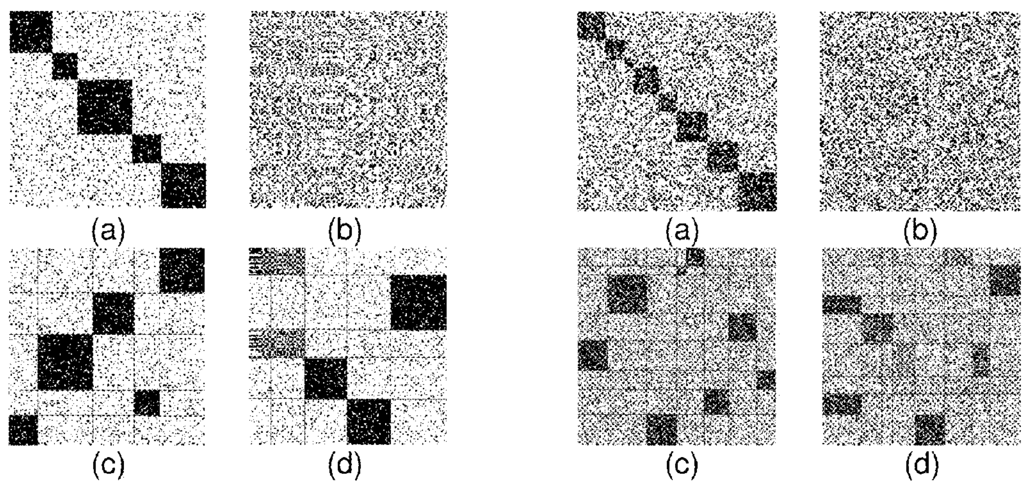
FIG. 10A
FIG. 10B

IDENTIFYING RELATIONSHIPS BETWEEN ENTITIES USING TWO-DIMENSIONAL ARRAY OF SCALAR ELEMENTS, AND A BLOCK MATRIX

PRIORITY

This application claims priority to Great Britain Patent Application No. 1221497.9, filed Nov. 29, 2012, and all the benefits accruing therefrom under 35 U.S.C. §119, the contents of which in its entirety are herein incorporated by reference.

BACKGROUND

The invention relates in general to the field of computer-implemented methods for identifying, managing and displaying a large set of relationships between entities. In particular, it relates to co-clustering methods.

Graphs are a popular data representation for modeling relationships, connections, etc., between entities. For example, bi-partite graphs have been the focus of a broad spectrum of studies spanning from document analysis to bioinformatics. A bi-partite graph paradigm may indeed be relied upon to represent various kinds of relationships, e.g., between parts of a computer-aided designed or CAD complex objects, real-world objects and attributes, etc., or even to represent data acquisition patterns between sets of processor cores and sets of data. Analysis of such related data is therefore of great importance for many companies, which accumulate increasingly large amounts of interaction data.

One common approach involves the identification of groups of objects or entities that share common properties, have similar attribute values, etc. The availability of such information is advantageous in many respects, as patterns can be detected, improper relations can be repaired or even anticipated.

Studies have suggested that matrix-based representations are more suitable and offer "superior readability" compared to node-link representations, particularly when analyzing large number of subjects/variables. In some cases, one has interest in visualizing thousands of subjects and several dozens to hundreds of variables, therefore a matrix representation can advantageously be adopted for bi-partite graphs. Given a matrix data representation, the problem of simultaneous group discovery across two data dimensions can be mapped to a matrix co-clustering instance. The goal is to reveal the latent structure of a seemingly unordered matrix. This is achieved by discovering a permutation of matrix rows and columns, and a respective grouping, such that the resulting matrix is as homogeneous as possible. In a typical setting as contemplated herein, the rows represent the subjects (CAD objects or parts, cores, etc.) and the columns identify the variables (other entities to which the subject entities relate, attribute values, data accessed by a given processor, etc.).

Presently, techniques for matrix co-clustering are predominantly based either on hierarchical clustering or on spectral clustering principles. As we discuss in more detail later on, both approaches exhibit limited scalability. The aim of the present approach is to provide a highly scalable approach that supports the analysis of thousands of graph nodes, and can easily drive interactive visual interfaces.

The principle of co-clustering was introduced first by Hartigan with the goal of 'clustering cases and variables simultaneously'. Initial applications were for the analysis of voting data. Since then, several co-clustering algorithms have been proposed, broadly belonging into two classes, based on: a) hierarchical clustering, and b) spectral clustering.

Agglomerative hierarchical clustering approaches are widely used in biological and medical sciences. In this setting, co-clustering also appears under the term 'bi-clustering'. One application is for the analysis of gene expression profiles. Columns and rows of an expression profile matrix are sorted using the relative orders of the leaves of the corresponding dendrograms constructed for genes and for arrays. The reordering of the dendrogram leaf objects is called seriation. Hierarchical clustering approaches can lead to discovery of very compact clusters. However, this comes at a high runtime complexity, i.e., ranging from $O(n^2)$ to $O(n^2 \log^2 n)$—n being the number of objects—depending on the agglomeration process. Therefore, their applicability is limited to data instances that typically do not exceed several hundreds of objects. Such approaches are deemed prohibitive, even for today's computers, if one considers interactive response times.

Spectral co-clustering approaches view the co-clustering problem as an instance of graph partitioning. Essentially, the problem is relegated to an eigenvector computation. Spectral clustering approaches are powerful for detecting non-linear cluster relationships (e.g., concentric circles). However, for some cases, including those contemplated here, one is interested in detecting rectangular clusters; hence, it can be realized that computationally simpler techniques may also discover the existence of rectangular co-clusters. The complexity of spectral approaches is in the order of $O(n \log^2 n)$. Recent works report a runtime of several seconds for a few thousands of objects; as such, their usefulness is typically limited to small data instances (fewer than $10^4$ nodes).

In the last years, approaches have appeared that view co-clustering from a purely optimization perspective and do cluster assignments using an information theoretic objective function. So, the optimal co-clustering maximizes the mutual information between the clustered random variables.

In the field of visualization, several techniques have been proposed for visualizing bipartite graphs. Such approaches do usually not involve co-clustering.

Finally, there exist approaches that encapsulate hybrid visualization methods, using a combination of matrix and node-link techniques, so as to accommodate a more holistic graph exploration experience.

SUMMARY

In one embodiment, a computer-implemented method for identifying relationships between entities includes accessing a first data structure being a two-dimensional array of scalar elements ($e$, $e_{ij}$, $e_{kl}^{(i)}$) representable as a matrix, each of the scalar elements capturing a relationship between two entities; reorganizing the first data structure by clustering the scalar elements separately on each dimension of the two-dimensional array, to obtain a second data structure, representable as a K×M block matrix, which is an arrangement of rows and columns of blocks, wherein each block is a reordered sequence of rows and/or columns of the first data structure; compacting the second data structure by: determining two parallel block sequences, which are the most similar according to a given distance measure, the parallel block sequences being either distinct rows or distinct columns of blocks of the second data structure; and reorganizing the second data structure by merging the two determined sequences into a single block sequence, wherein the $n^{th}$ block of the single sequence is the union of: the $n^{th}$ block of a first one of the two parallel sequences; and the $n^{th}$ block of a second one of the two parallel sequences, wherein a compacted data structure is obtained which is representable as a K−1×M or a K×M−1 block matrix; repeating the compacting, using a compacted data structure as input, in place of the second data structure; and identifying, in a graphical user interface, one or more blocks of a compacted data structure and/or selected scalar elements therein.

BRIEF DESCRIPTION OF THE SEVERAL VIEWS OF THE DRAWINGS

FIG. 9 is a graph comparing runtime performances of an embodiment of the invention vs. a spectral co-clustering approach; and FIGS. 10A and 10B show a comparison of present methods (in embodiments which automatically determine the number of final co-clusters) with spectral-based methods (requiring as input the number of co-clusters).

DETAILED DESCRIPTION

Figure 1:
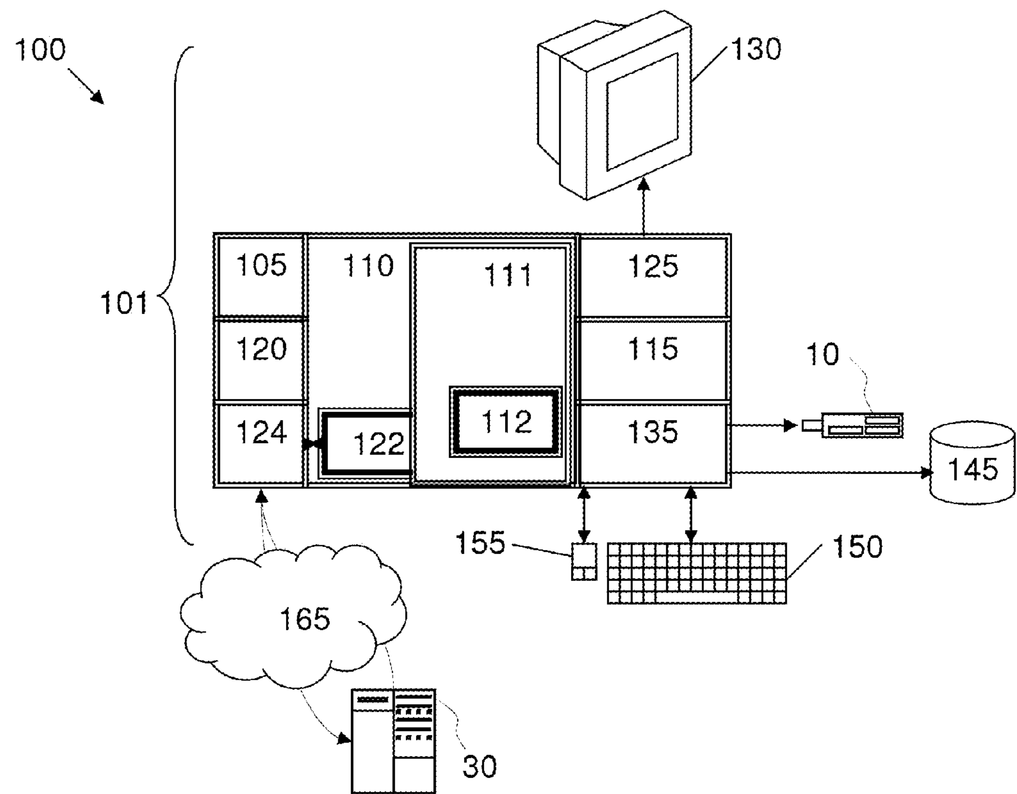
FIG. 1 represents a general purpose computerized system, suited for implementing one or more method steps as involved in embodiments of the invention.
Figure 2A:
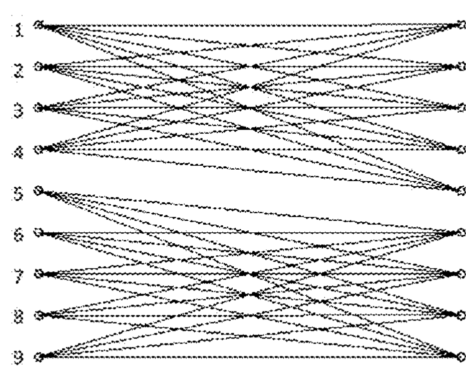
FIG. 2A shows a typical example of a bipartite graph representation.
Figure 2B:
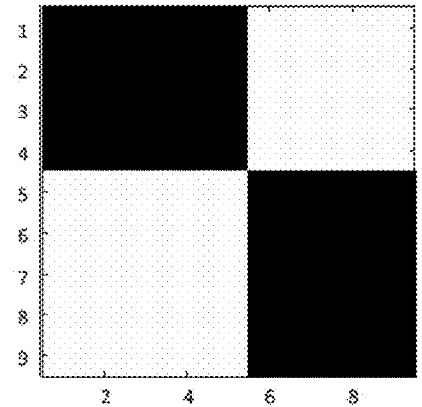
FIG. 2B is an adjacency matrix representation of the same relationships as captured in the bipartite graph representation of FIG. 2A.

According to a first aspect, the present invention is embodied as a computer-implemented method for identifying relationships between entities, the method including accessing a first data structure being a two-dimensional array of scalar elements representable as a matrix, each of the scalar elements capturing a relationship between two entities; reorganizing the first data structure by clustering the scalar elements separately on each dimension of the two-dimensional array, to obtain a second data structure, representable as a K×M block matrix, which is an arrangement of rows and columns of blocks, wherein each block is a reordered sequence of rows and/or columns of the first data structure; compacting the second data structure by determining two parallel block sequences, which are the most similar according to a given distance measure, the parallel block sequences being either distinct rows or distinct columns of blocks of the second data structure; and reorganizing the second data structure by merging the two determined sequences into a single block sequence, wherein the $n^{th}$ block of the single sequence is the union of the $n^{th}$ block of a first one of the two parallel sequences and the $n^{th}$ block of a second one of the two parallel sequences, whereby a compacted data structure is obtained which is representable as a K−1×M or a K×M−1 block matrix; repeating the step of compacting, using a compacted data structure as input, in place of the second data structure; and identifying, in a graphical user interface, one or more blocks of a compacted data structure and/or selected scalar elements therein.

In embodiments, the parallel block sequences determined are merged into a single block sequences if a final entropy of the single block sequence as after merging is reduced compared to an initial entropy of the parallel block sequences before merging, each of the initial entropy and the final entropy normalized according to the respective numbers of blocks involved.

Each of the initial and final entropies is computed according to normalized intra-block densities, an intra-block density of a given block being computed based on an average value of the scalar elements in the given block.

In exemplary embodiments, the final entropy computed is proportional to $$\frac{-\sum_{i=1,K} p_i \log p_i}{\log K},$$

where i runs over each block within a sequence containing K blocks, and $p_i$ is the $i^{th}$ of the normalized intra-block densities.

The initial entropy of the parallel block sequences is proportional to $$\frac{-\sum_{i=1,2K} p_i \log p_i}{\log 2K},$$

where i runs over each block of the two parallel block sequences, containing 2K blocks in total.

In embodiments, identifying the two parallel block sequences comprises computing distances between blocks of the parallel block sequences, based on intra-block densities, and more specifically, distances between parallel block sequences are computed as an $L_2$-Norm of the intra-block densities.

The first data structure accessed is a two-dimensional array of scalar elements, which captures relationships between at least $10^4$ entities, more specifically $10^5$ entities In exemplary embodiments, the first data structure accessed comprises scalar elements being binary or real-number values. The first data structure accessed is representable as an adjacency matrix of a bipartite graph, a bipartite graph of entities versus entity attributes. In embodiments, the step of reorganizing uses a K-means++ algorithm.

According to another aspect, the invention is embodied as a computer-implemented method for identifying an abnormal relationship between two entities, comprising all the steps of the method according to any one of the above embodiments, and wherein identifying includes identifying a given scalar element in a given block of a compacted data structure, which has a value departing from an average value of the scalar elements of the given block as well as the two entities linked by the relationship captured by the a given scalar element.

According to still another aspect, the invention is embodied as a method of resolving an abnormal relationship between two entities, comprising all the steps of the previous method, and further including changing a real-world relationship, linking two real-world entities, and corresponding to the relationship captured by the a given scalar element, such that the real-world relationship corresponds to a value not anymore departing from the average value of the scalar elements of the given block.

Any of the above methods may comprise, at the step of "identifying", either or both of the following: displaying a graphical representation of one or more dense blocks of a compacted data structure, and emphasizing the one or more dense blocks to a user; and/or emphasizing one or more scalar elements of one or more dense blocks of a compacted data structure, which one or more scalar elements have values departing from average values of scalar elements of the one or more dense blocks, by displaying a negative of the one or more dense blocks.

According to another aspect, the invention is embodied as a computer program product comprising a computer-readable storage medium having computer-readable program code embodied therewith, the computer-readable program code configured to implement all of steps of a method as recited above.

Devices, systems and methods embodying the present invention will now be described, by way of non-limiting examples, and in reference to the accompanying drawings.

The following description is structured as follows. First, general embodiments and high-level variants are described (sect. 1). The next section addresses more specific embodiments and technical implementation details (sect. 2).

1. General Embodiments and High-Level Variants

FIG. 1 represents a general computerized system, suited for implementing method steps as involved in embodiments of the invention.

It will be appreciated that the methods described herein are at least partly non-interactive, and automated by way of computerized systems, such as servers or embedded systems. In exemplary embodiments though, the methods described herein can be implemented in a (partly) interactive system. These methods can further be implemented in software 112, 122 (including firmware 122), hardware 105, or a combination thereof. In exemplary embodiments, the methods described herein are implemented in software, as an executable program, and is executed by a special or general-purpose digital computer, such as a personal computer, workstation, minicomputer, or mainframe computer. The most general system 100 therefore includes a general-purpose computer 101.

In exemplary embodiments, in terms of hardware architecture, as shown in FIG. 1, the computer 101 includes a processor 105, memory 110 coupled to a memory controller 115, and one or more input and/or output (I/O) devices (or peripherals) 10, 145 that are communicatively coupled via a local input/output controller 135. The input/output controller 135 can be, but is not limited to, one or more buses or other wired or wireless connections, as is known in the art. The input/output controller 135 may have additional elements, which are omitted for simplicity, such as controllers, buffers (caches), drivers, repeaters, and receivers, to enable communications. Further, the local interface may include address, control, and/or data connections to enable appropriate communications among the aforementioned components. As described herein the I/O devices 10, 145 may generally include any generalized cryptographic card or smart card known in the art.

The processor 105 is a hardware device for executing software, particularly that stored in memory 110. The processor 105 can be any custom made or commercially available processor, a central processing unit (CPU), an auxiliary processor among several processors associated with the computer 101, a semiconductor based microprocessor (in the form of a microchip or chip set), a macroprocessor, or generally any device for executing software instructions.

The memory 110 can include any one or combination of volatile memory elements (e.g., random access memory (RAM, such as DRAM, SRAM, SDRAM, etc.)) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 110 may incorporate electronic, magnetic, optical, and/or other types of storage media. Note that the memory 110 can have a distributed architecture, where various components are situated remote from one another, but can be accessed by the processor 105.

The software in memory 110 may include one or more separate programs, each of which comprises an ordered listing of executable instructions for implementing logical functions, notably functions involved in embodiments of this invention. In the example of FIG. 1, software in the memory 110 includes instructions 112 for implementing method for identifying relationships between entities.

The software in memory 110 shall also typically include a suitable operating system (OS) 111. The OS 111 essentially controls the execution of other computer programs, such as possibly software 112 for implementing methods as described herein.

The methods described herein may be in the form of a source program 112, executable program 112 (object code), script, or any other entity comprising a set of instructions 112 to be performed. When a source program, then the program needs to be translated via a compiler, assembler, interpreter, or the like, which may or may not be included within the memory 110, so as to operate properly in connection with the OS 111. Furthermore, the methods can be written as an object oriented programming language, which has classes of data and methods, or a procedure programming language, which has routines, subroutines, and/or functions.

In exemplary embodiments, a conventional keyboard 150 and mouse 155 can be coupled to the input/output controller 135. Other output devices such as the I/O devices 145 may include input devices, for example but not limited to a printer, a scanner, microphone, and the like. Finally, the I/O devices 10, 145 may further include devices that communicate both inputs and outputs, for instance but not limited to, a network interface card (NIC) or modulator/demodulator (for accessing other files, devices, systems, or a network), a radio frequency (RF) or other transceiver, a telephonic interface, a bridge, a router, and the like. The I/O devices 140, 145 can be any generalized cryptographic card or smart card known in the art. The system 100 can further include a display controller 125 coupled to a display 130. In exemplary embodiments, the system 100 can further include a network interface 160 for coupling to a network 165. The network 165 can be an IP-based network for communication between the computer 101 and any external server, client and the like via a broadband connection. The network 165 transmits and receives data between the computer 101 and external systems 30, which can be involved to perform part or all of the steps of the methods discussed herein. In exemplary embodiments, network 165 can be a managed IP network administered by a service provider. The network 165 may be implemented in a wireless fashion, e.g., using wireless protocols and technologies, such as WiFi, WiMax, etc. The network 165 can also be a packet-switched network such as a local area network, wide area network, metropolitan area network, Internet network, or other similar type of network environment. The network 165 may be a fixed wireless network, a wireless local area network (LAN), a wireless wide area network (WAN) a personal area network (PAN), a virtual private network (VPN), intranet or other suitable network system and includes equipment for receiving and transmitting signals.

If the computer 101 is a PC, workstation, intelligent device or the like, the software in the memory 110 may further include a basic input output system (BIOS) 122. The BIOS is a set of essential software routines that initialize and test hardware at startup, start the OS 111, and support the transfer of data among the hardware devices. The BIOS is stored in ROM so that the BIOS can be executed when the computer 101 is activated.

When the computer 101 is in operation, the processor 105 is configured to execute software 112 stored within the memory 110, to communicate data to and from the memory 110, and to generally control operations of the computer 101 pursuant to the software. The methods described herein and the OS 111, in whole or in part, but typically the latter, are read by the processor 105, possibly buffered within the processor 105, and then executed.

When the systems and methods described herein are implemented in software 112, as is shown in FIG. 1, the methods can be stored on any computer readable medium, such as storage 120, for use by or in connection with any computer related system or method.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer 30 or entirely on the remote computer or server 30. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the appended Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Figure 3:
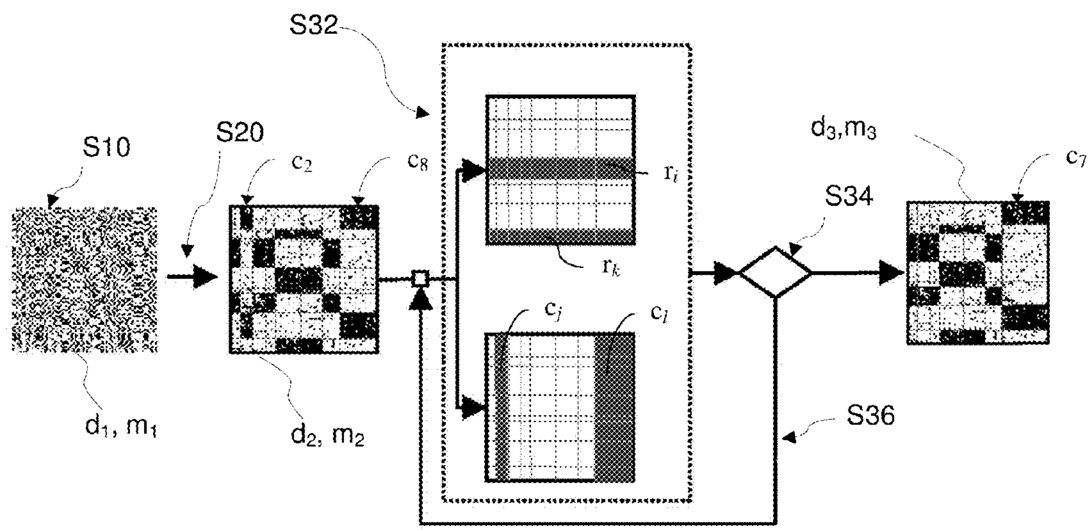
FIG. 3 is a flowchart diagram illustrating steps and components involved in a method for identifying relationships between entities, according to embodiments.
Figure 4:
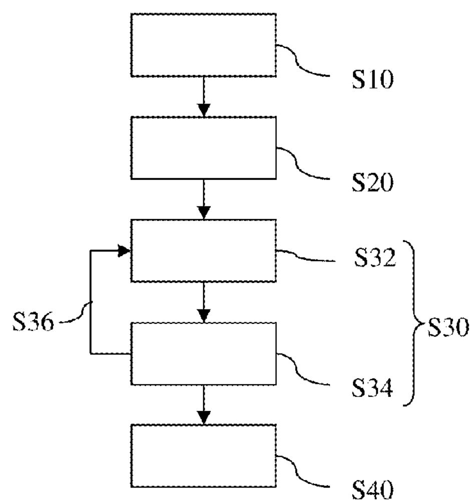
FIG. 4 is a flowchart showing only the succession of steps involved in FIG. 3.

Referring now generally to FIGS. 1 to 10, and more particularly to FIGS. 3 and 4, an aspect of the invention is first described, which concerns computer-implemented methods for identifying relationships between entities, and in particular to detect abnormal or missing relationships between entities.

First, such methods comprise: accessing (block S10) a first data structure $d_1$, i.e., an input data structure that encodes a two-dimensional array of scalar elements, which is representable as a matrix $m_1$, and whose scalar elements capture relationships between pairs of entities, for example real-world entities (like CAD parts/objects of a products to be manufactured, etc.). In specific embodiments, the first data structure accessed corresponds to an adjacency matrix of a bipartite graph, e.g., a bipartite graph of entities versus entities, subjects vs. variables, or objects vs. attributes, etc. Note that, in variants, this matrix may be an incidence matrix or any other suitable type of matrices.

Scalar elements typically comprise numerical values, i.e., binary (0 or 1), real, complex numbers or even strings, or more generally anything that can be converted to numbers for a sensible comparison. This value relates a subject $s_i$ to a variable $v_j$, or more generally two entities $s_i$, $v_j$, such that a single scalar element may be noted e.g., $\{s_i, v_j, e_{ij}\}$ or simply $e_{ij}$, where $e_{ij}$ is a value that "connects" the $i^{th}$ and $j^{th}$ entities in the initial data structure $d_1$. For instance, the simplest relationships are likely of binary form, as used in the appended (for sake of pedagogy and simplicity), with e.g., a value of 1 meaning that there is a relation between two entities, while 0 indicates no known relation. In the appended drawings, a black dot is typically representative of a "1". More complex relations can however be captured by real values, where the actual value indicates e.g., an intensity of the relation, a polarization of dynamic of the relation (thanks to +/− sign), etc. For example, for CAD parts, a 0.0 (or 0) may denote a relation "is in contact with", while a non-zero value may denote an actual distance to another part. Negative values may denote a penetration distance into another part, etc. More complex relationships could still be captured thanks to complex numbers, a thing that incidentally would not prevent from calculating intra-block densities as discussed later, e.g., based on sum of absolute values of the scalar elements.

Only for the non-zero scalar element $\{s_i, v_j, e_{ij}\}$ are tracked and stored in the various data structures along the co-clustering process and/or the compacting steps, since the value of the remaining elements is known by default. The latter can thus simply be skipped, which is advantageous in terms of memory space required for the data structures. This is all the more advantageous for binary values, all the more for sparse arrays.

No orderly format is required for the entities as input; rather entities (subjects and variables) and relations are typically at random.

Next, the input data structure shall be reorganized (block S20), which operation is performed by clustering the scalar elements separately on each dimension of the two-dimensional array $d_1$. What is done at this stage is essentially similar to known co-clustering step, it being noted that the separate clustering process on each dimension results in a linear complexity. Co-clustering, also known as biclustering or two-mode clustering is a technique that enables simultaneous clustering of rows and columns of a matrix. Given an input matrix, a co-clustering algorithm generates co-clusters, i.e., subsets of rows which exhibit similar behavior across subsets of columns, or vice versa (please check definition). Block S20 may for instance uses a K-means algorithm, more specifically a K-means++ algorithm, or the like. This step leads to a second data structure $d_2$, which is representable as a K×M block matrix $m_2$. Typically, square matrices are used such that in fact M=K, and a K×K block matrix results. As immediately apparent from FIG. 3, 5 or 6, a block matrix $m_2$ can be described as an arrangement of rows and columns of blocks. Owing to the previous reorganization block (S20), each block is a reordered sequence of rows and/or columns of the first data structure $d_1$. Yet, since in general the first data structure $d_1$ is not ordered, the reordered sequence obtained is a reordered sequence of both rows and columns of the first data structure $d_1$.

After this first reorganization (or co-clustering) step, the methods shall compare rows or columns of blocks, to identify the closest pair of rows or columns, and merge them blockwise, into a new, single sequence. At this point, and as opposed to prior art approaches, the "atoms" are not scalar elements anymore but blocks of scalar elements, i.e., reordered subsets of the first data structure $d_1$.

More precisely, the second data structure $d_2$ is compacted (block S30) in a two-stage process, which decomposes into:

Determining (subblock S32) the two parallel block sequences $r_i$ and $r_k$ or $c_j$ and $c_l$, which are the most similar, e.g., according to a given distance measure. The parallel block sequences correspond either to two distinct rows or two distinct columns of blocks, as seen in FIG. 3. A sequence of blocks otherwise corresponding to a vector or co-vector of the second two-dimensional data structure $d_2$; and Reorganizing S34 the second data structure $d_2$. The reorganization S34 essentially revolves around:

merging the two determined sequences into a single block sequence, wherein the $n^{th}$ block of the single sequence is the union of the $n^{th}$ block of a first one of the two parallel sequences; and the $n^{th}$ block of a second one of the two parallel sequences.

Each block of the single sequence defined is thus the union of two blocks, whose scalar elements are thus unified into a single set forming a new block. The two blocks at stake are, graphically speaking, in vis-à-vis in the pair of rows or columns that were determined to be the most similar.

A compacted data structure $d_3$ is accordingly obtained, which, depending on whether two rows or two columns were merged, is representable as a K−1×M or a K×M−1 block matrix, respectively. As for instance illustrated in FIG. 3, a given compacting step, using $d_2$ as input shall result in $d_3$. At each block S32, it is considered whether to merge two columns or two rows, whichever are the closest. For the sake of exemplification, it was assumed in FIG. 3 that the columns $c_2$ and $c_8$ have been found to be the most similar sequences of $d_2$. Columns $c_2$ and $c_8$ are thus merged into a new column, which can be referred to as new column $c_7$ in $d_3$. Note that $d_3$ (or its graphical matrix representation $m_3$) in FIG. 3 is not the very final compacted data structure as the process would likely repeat, as needed, block S36, to results in progressively more compacted data structures. How many times the compacting is repeated (block S36) and the criterion used for merging pairs of sequences shall be discussed later in detail.

When repeating (the first time) the compacting, the compacted data structure $d_3$ shall be used as input, in place of the second data structure $d_2$, leading to a further compacted data structure $d_4$, etc., which eventually results in a K'×M' block matrix, where K' and M' are such that K−K'+M−M' is equal to the number of times the compacting was carried out.

Figure 8:
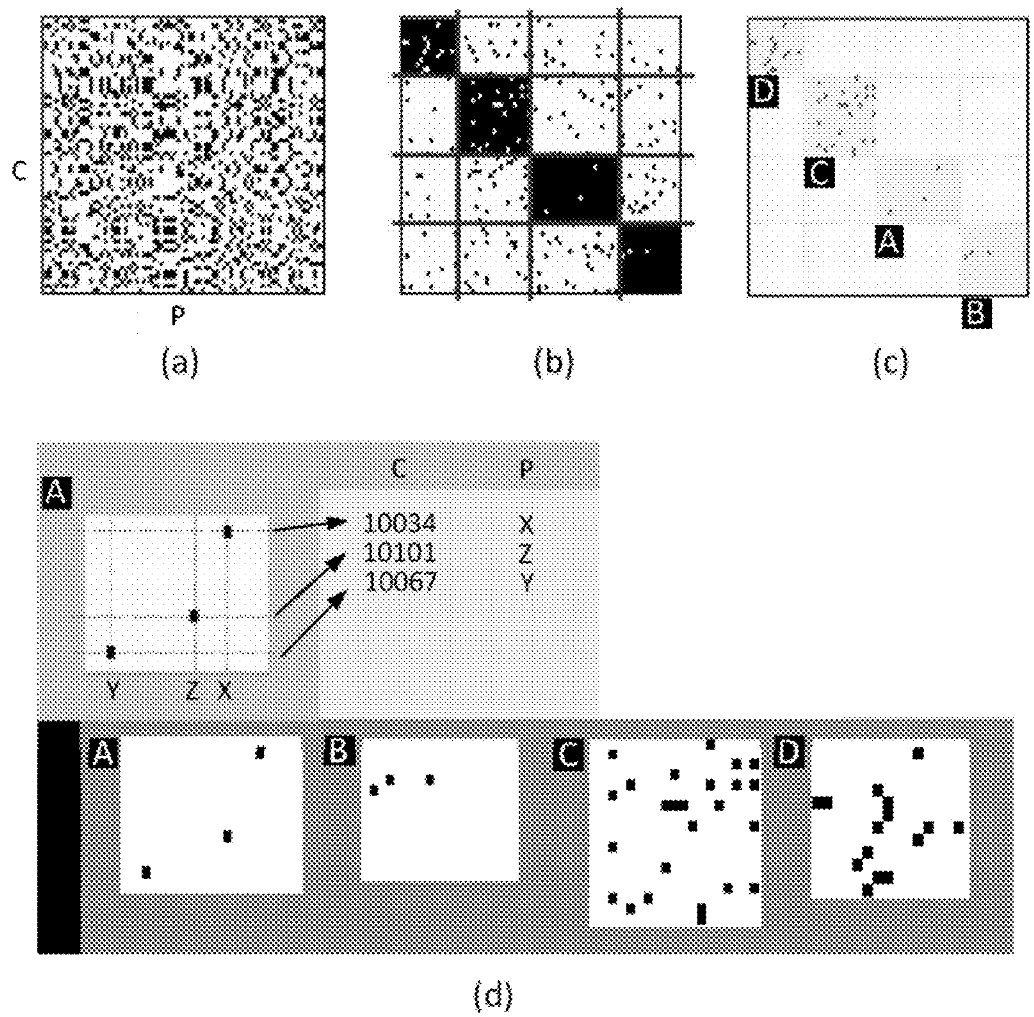
FIG. 8 illustrates examples of a graphical interface displaying dense blocks of a compacted data structure as well as selected scalar elements thereof, the elements capturing relationships between pairs of (real-world) entities, as in embodiments.

Finally, one or more blocks of a resulting compacted data structure and/or selected scalar elements therein shall be identified (block S40) by the method, and identified to a user via a suited graphical user interface (GUI), as illustrated in FIG. 8.

For example, only the densest blocks of a final (or intermediate) compacted data structure could be displayed, or at least emphasis could be put on such blocks, as illustrated in FIG. 8(B). More instructive, selected scalar elements can be emphasized, as in FIG. 8(C). These selected scalar elements may for instance be those scalar elements that have values departing from average values (of scalar elements) in their respective blocks, e.g., local deviances, extrema, statistical abnormalities, i.e., those scalar elements the farthest from the average block value. Most simply and visually appealing, the GUI may display a negative of the dense blocks, as shown in FIG. 8(C), which results in visually emphasizing the few scalar elements with values departing from the average block values.

The emphasized scalar elements could for instance be user selectable to interactively display associated characteristics, like the two entities connected by the scalar elements, as illustrated in FIG. 8(*d*)(A). In this example, the successive selection of either of the scalar elements displayed in the left panel of FIG. 8(*d*)(A) results in displaying associated characteristics (reference of entity C vs. entity P) in the right panel of FIG. 8(*d*)(A). In variants, the local deviances could be detected automatically, and their associated characteristics displayed in the GUI.

Example of matrix representations of the compacted co-clusters obtained are shown in FIGS. 3, 5, 6, 7, 8, and 10. In these examples (all using binary scalar element values), existence of a '1' (black dot) means that an entity is linked to another entity (e.g., a given CAD part is "in contact" with another CAD part), otherwise the value is '0 (white dot). It is quite evident in these cases, especially where a large set of entities is involved, that a reordered matrix view provides strong evidence on the existence of patterns in the data.

At present, the merging process is explained in more details: After the first reorganization (co-clustering) block S20, the method compares pairs of rows or columns of blocks, to identify the closest pair of rows or columns, and merge them blockwise, into a new, single sequence. Not only this results in harmonious clusters (see e.g., FIGS. 5-7), i.e., the apparent complexity for the user of the data structure is reduced, but also the complexity of the data structure as stored by the system is reduced too, at each compacting. The compacted data structures can be stored by the system, typically in RAM, as this is enabled by the present methods even for ~$10^8$ or $10^{10}$ scalar elements.

For example, consider two particular block sequences $c_2$ and $c_8$ (i.e., columns 2 and 8 in FIG. 3) as resulting from block S20:

$$c_2=\{b_{21}, b_{22}, \ldots, b_{28}\}; \text{ and} \quad \text{(Eq. 1)}$$

$$c_8=\{b_{81}, b_{82}, \ldots, b_{88}\}. \quad \text{(Eq. 2)}$$

In these notations, $b_{ij}$ denotes block i, j while $c_i$ denotes the $i^{th}$ column of blocks in the data structure $d_2$. As touched earlier, each block $b_{ij}$ corresponds to a two-dimensional array of scalar elements, i.e., a subset of the initial array $d_1$, which subset comprises re-ordered scalar elements of the initial array $d_1$. As a result of the initial co-clustering block S20, the block sequence may for instance be stored in a block data structure $$c_1\{c_1, c_2, \ldots, c_8\}=\{\{b_{11}, b_{12}, \ldots, b_{18}\}, \{b_{21}, b_{22}, \ldots, b_{28}\}, \ldots, \{b_{81}, b_{82}, \ldots, b_{88}\}\}. \quad \text{(Eq. 3)}$$

Assume now that the block sequences $c_2$ and $c_8$ are found to be the closest to each other, e.g., the average densities of the $n^{th}$ blocks in each sequence remains close enough to each other: then the above data structure may thus be compacted at block S30 as $$\{\{b_{11}, b_{12}, \ldots, b_{18}\}, \{b_{31}, b_{32}, \ldots, b_{38}\}, \ldots, \{b_{21}\cup b_{81}, b_{22}\cup b_{82}, \ldots, b_{28}\cup b_{88}\}\}. \quad \text{(Eq. 4)}$$

In other words, one of the column vector has disappeared (namely $c_2=\{b_{21}, b_{22}, \ldots, b_{28}\}$ in this example), while a new column $\{b_{21}\cup b_{81}, b_{22}\cup b_{82}, \ldots, b_{28}\cup b_{88}\}$ has replaced the initial column $c_8$, which new column effectively becomes the new column $c_7$, in the compacted data structure $d_3$, as indicated in FIG. 3. It is however unimportant how a sequence is re-labeled or where a final merged sequence is located, although it may be inserted in proximity of another, yet similar column, as made possible from a previous calculation of distance matrix.

The data structure is thus progressively compacted. Indeed, as illustrated in the above example, although the number of scalar elements remains unchanged, the number of column vectors (and row vectors likewise) decreases during the compacting process, such that the stored compacted data structure $d_n$ gets progressively simplified.

As to be discussed later in detail, only a small number of compacting steps (e.g., 10) is typically needed: such steps operate at a block level instead of at a scalar element level, which makes the present methods markedly faster than prior art's.

Incidentally, the proximity of neighboring scalar element values as progressively obtained in each block makes them suitable for data compression, if needed, e.g., by way of delta encoding and subsequent compression. Thus, each block could be compressed, at any step, e.g., the final step or any or each intermediate step, but at a final step for transferring a result of the clustering process.

Another main contribution of the present invention concerns the criterion used to decide whether to merge two parallel block sequences. In some basic implementations, this could be decided at each compacting step by the user herself, using any suited subjective or objective criterion. Since only a few compacting blocks S30 are likely involved with the above method, the user involvement remains moderate. However, it has been found that an objective criterion could advantageously be used, which relies on an appropriate information theoretic function (or entropy-based), such that the compacting process can execute and terminate without the user having first to enter a pre-determined number of cycles or final clusters, as required in prior art methods. Meanwhile, the choice of such a function can be optimized, so as to provide homogeneous and visually convincing clusters, and this in a small number of compacting steps only, as to be discussed now.

Figure 7:
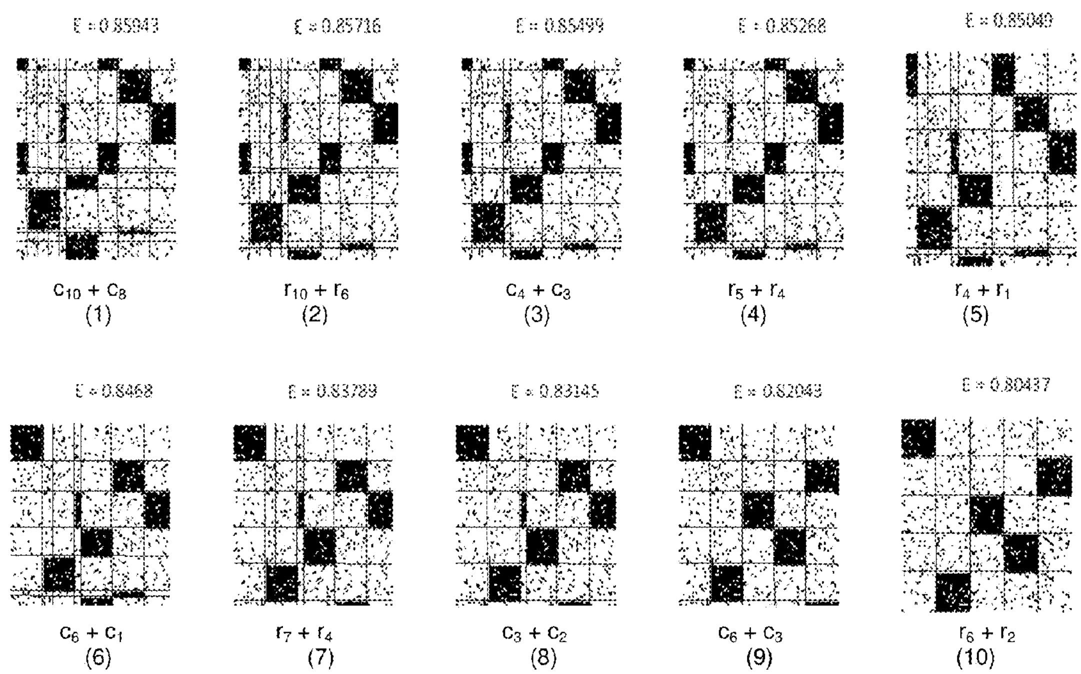
FIG. 7 illustrates, graphically, ten intermediate steps to compact the input matrix of FIG. 6 (left) and arrive at the final matrix of FIG. 6 (right), and the corresponding minimization of an information theoretic objective function E, as in embodiments.

Referring more particularly to FIG. 7, embodiments of the present invention therefore make use of the following criterion: the most similar parallel block sequences (determined at block S32) are merged (block S34) into a single block sequences if a value of entropy of the single block sequence (as obtained after merging) is reduced compared to an initial entropy value, i.e., the entropy of the parallel block sequences (as before merging), where each entropy value is normalized according to the number of blocks involved in each case; this shall be exemplified below.

For example, each of the initial and final entropies can be computed according to normalized intra-block densities $p_i$, where the intra-block density, i.e., the density pertaining to a given block is calculated using (e.g., proportional to) an average value of the scalar elements in the given block. In other words, the relationships between entities can be turned into values, which in turn determine densities of the blocks, whereby an objective criterion is available, which is directly, yet logically linked to the relationships between entities. Note that the average value of the scalar elements in a given block can be calculated according to various normalization schemes. Should the case permits, e.g., if the scalar elements are complex numbers, absolute values or square modulus of the scalar elements may be used to calculate the intra-block densities. In the simplest cases (e.g., binary or real positive values), an intra-block density 92$_i$ (not yet normalized) of a $i^{th}$ block is taken as $$\rho_i = \frac{1}{n_i}\sum_{k,l} e_{kl}^{(i)}, \qquad \text{(Eq. 5)}$$

where the sum runs over each value of scalar elements $e_{kl}^{(i)}$ in this $i^{th}$ block is divided by $n_i$, i.e., the size of block i, that is, number of scalar elements in block i. As discussed in the next part, intra-block densities $\rho_i$ may be conveniently normalized by dividing by:

$$\rho_{sum} = \sum_{i=1,K} \rho_i, \qquad \text{(Eq. 6)}$$

Which leads to normalized intra-block densities (i.e., probabilities) $p_i$:

$$p_i = \frac{1}{n_i \rho_{sum}}\sum_{k,l} e_{kl}^{(i)}. \qquad \text{(Eq. 7)}$$

Then, the final entropy computed is proportional to:

$$\frac{-\sum_{i=1,K} p_i \log p_i}{\log K}, \qquad \text{(Eq. 8)}$$

where i runs over each block within a sequence containing K blocks, and $p_i$ is the $i^{th}$ intra-block density.

This definition of the final entropy makes the objective function proportional to an usual information entropy and thus can be called an entropy. It is yet normalized by log K, i.e., by the logarithm of the number K of blocks in the sequence. Thus, the entropy is normalized according to the number of blocks involved in the sequence.

Similarly, the initial entropy of the parallel block sequences can be chosen proportional to:

$$\frac{-\sum_{i=1,2K} p_i \log p_i}{\log 2K}, \qquad \text{(Eq. 9)}$$

where i runs over each block of the two parallel block sequences, containing 2K blocks in total. This definition is equivalent to that of the final entropy, if one considers that the parallel block sequences form a single super sequence, with one of the sequences appended to the other. In variants, the initial entropy could be calculated separately for each of the parallel block sequences (using a definition equivalent to that of the final entropy), and then averaged, for comparing to the final entropy. Other size consistent definitions of the objective function, the entropy, could be devised. An advantage of the above definitions is that they require a minimal number of operations, primarily determined by the number of blocks in the sequences considered.

Figure 6:
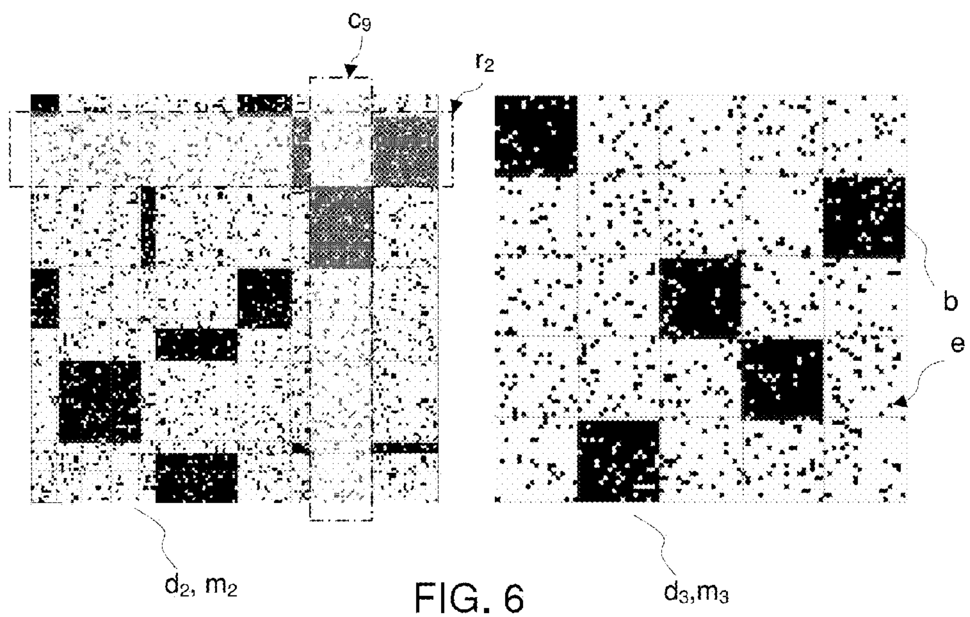
FIG. 6 shows an example of an input matrix (left) and a final matrix representation (right) of a data structure compacted according to embodiments.

Thanks to such normalization choices, both the initial and final entropies are directly comparable, independently from the number of blocks involved in each case. Thus a single operation e.g., a difference is needed in order to decide whether to merge two sequences or not. This operation is performed at block S34 in FIG. 3 or 4. If the entropy is reduced, the two sequences determined are effectively merged and the process loops back to block S32, where a new pair of sequences shall be considered for merging. If the entropy is not reduced, then the compacting process stops and the compacted structure having the lowest entropy is retained, and displayed in the GUI. This process is exemplified in FIGS. 6 and 7: FIG. 6 shows an example of an input matrix (left) together with a final matrix representation (right) of a compacted data structure, whereas FIG. 7 illustrates the (ten) intermediate steps that were needed to arrive at the final matrix of FIG. 6. FIG. 7 further shows entropy values E calculated at each step. The pair of rows or column which have been merged are indicated under each figure. For example, the tenth and final compacting step results in the block matrix depicted in FIG. 7(10): this final block matrix was obtained by merging rows $r_6+r_2$ of the matrix of FIG. 7(9), that is, the second and last rows of FIG. 7(9) (counting from the upper row). Similarly, FIG. 7(9) was obtained by merging columns $c_6+c_3$ (counting from the leftmost column) of FIG. 7(8), etc.

In embodiments, the identification of a candidate pair of parallel block sequences, block S32, requires computing distances between blocks of the parallel block sequences, e.g., based on intra-block densities. For example, distances between parallel block sequences are computed as a $L_2$-Norm of the intra-block densities. Yet, any $L_q$-Norm ($0<q<\infty$) can be contemplated, starting with the $L_1$-Norm. Another possibility would be to use a correlation (i.e., normalized $L_2$). More generally, any linear distance function should produce satisfying results since here one wants to capture the similarity between parallel blocks. Now, it is believed that regular $L_1$- and $L_2$-Norms may be the most meaningful approaches in the present context.

A step of compacting comprises an initial step of computing or updating intra-block densities pertaining to blocks of a data structure used as input. Then, two distance matrices are computed for rows and columns, respectively, and the two sequences that are the closest (be it two rows or two columns) are thus easily identified.

Present embodiments allows to compact arrays of relationships between up to at least $10^4$ entities, possibly $10^5$ entities (or nodes), and perhaps more (not tested). This imply about $10^8$ or $10^{10}$ scalar elements to be re-ordered, a things that would be properly impossible with prior art methods.

Present methods have a number of potential applications. For instance, referring more particularly to FIG. 8, another aspect of the present invention concerns methods for identifying abnormal relationships between entities. Such methods use the same steps as described earlier. Here, however, block S40 may focus on identifying, e.g., emphasizing scalar elements of a compacted data structure (call it $d_3$, irrespectively of the number of compacting steps required to achieve it), whose values significantly depart from the average block values. The associated entities, i.e., linked by the relationships captured by the scalar elements are identified as well, as illustrated in FIG. 8(*d*)(A). As per construction of the present methods, the identified spots are statistical exceptions, and in this sense are anomalies. This prompts the user to question, repair, amend, etc., the corresponding relationships, and possibly act on the entities themselves. For example, the present cluster techniques can be applied for diagnosis purposes, e.g., to detect missing, erroneous or sub-optimal specifications, e.g., in CAD applications, or, still, as another example, erroneous or sub-optimal parameter configuration of a computer or a computer power management unit, etc. Applications can also be found in bioengineering, biochemistry, biology, etc.

Then, a user can take steps to remedy such situations: This point precisely corresponds to another aspect of the present invention, which aims at resolving abnormal relationships between entities. Again, all the steps of the above methods can be implemented to that aim, except that, in addition, the user can now proceed to change the relationships, for instance real-world relationships, i.e., linking real-world entities. A user can take steps to remedy undesired situations, by changing or acting on these relationships or the entities (which effectively results in changing the relationships between entities), such that the updated relationships do not or would not anymore depart from average block values. For example, a suboptimal computer power management unit could be re-parameterized in order to optimize the power scheme. As another example, the present invention can be notably applied to optimizations of:

Photovoltaic systems, which include an array of photovoltaic modules, connected to each other (where the relationships may be the relative distances between the modules), Concentrated photovoltaic (CPV) systems, which similarly use various optics, or still, Photovoltaic thermal hybrid solar collectors (also "hybrid PV/T systems" or PVT), which are systems converting solar radiation into thermal and electrical energy, where, again, a number of parameters are involved, be it in the way the various components are inter-related (relative distance/positioning, power supply, etc.).

The above embodiments have been succinctly described in reference to the accompanying drawings and may accommodate a number of variants. Several combinations of the above features may be contemplated. Examples are given in the next section.

2. Specific Embodiments/Technical Implementation Details

As discussed in the previous section, main contributions of present embodiments revolve around:

Providing a fast, interactive solution for visualizing data co-clusters, which can be applied to various scenarios. As explained, the methodology consists in two main steps: an initial seeding and fast co-clustering step, followed by a refine step, which operates on a much smaller instance (block-level) of the problem. The co-clustering approach showcases linear complexity and is therefore suited for large interactive sessions. The approach lends itself to a simple implementation and is also highly amenable to parallelization. An inherent limitation of many co-clustering approaches is the explicit input of the parameter K—the number of clusters. Embodiments of the present invention do not impose such a requirement, and incorporate an automatic way of deriving an appropriate value of K, based on compressibility (entropy-based) arguments.

Embodiments can be leveraged for providing recommendations as to the relationships captured by the scalar elements. The clustering approach can be used as the foundation for a visual diagnostic & recommendation system. Recommendations may further be refined using, in addition to global patterns as discovered by the clustering process, personalized metrics attributed to individual entities.

A comprehensive empirical study with real and synthetic datasets was performed to validate: a) the scalability of the present approach, and b) the quality of the discovered clusters.

2.1 Overview of Specific Embodiments

Exemplary approaches are discussed hereafter, in reference to a particular application, for the sake of exemplification: the aim of this application is to optimize the allocation of (large) data chunks P vs. processor cores C (or simply "cores", for short), or more generally network nodes, etc. Let us assume a bipartite graph of nodes C versus data P, where the existence of an edge indicates that a core has accessed the particular data P. Data P could for instance be very large data chunks, distributed amongst a large set of nodes. Yet, the concept of entity pairs used herein could be applied to various types of pairs of entities, cast into subjects vs. variables, parameters vs. parameter values, etc., as discussed earlier. Thus, applications may notably extend to servers vs. clients, customers vs. products, etc. The information recorded in the graph can also been conveyed in an adjacency matrix, updated in real-time, if necessary, and containing the value of 'one' at position [i, j] if there exists an edge between the nodes i and j, otherwise the value is 'zero'. Note, that the use of the matrix metaphor also enables a more effective visualization of large graph instances.

This adjacency matrix, before any pre-processing, does not have an orderly format; the order of rows and columns is generally random. One goal is to extract the latent cluster structure from the matrix, and use this information to support recommendations as to which data should be brought closer to which computer node (in a computer node-centric approach) or which computer node should be allocated to the processing of which data chunks (in a data-centric approach). In other words, the aim is to provide recommendations (possibly accompanied by corresponding actions) as to some relationships between two types of entities (nodes vs. data). To that aim, one follows the methodology displayed in FIG. 8:

First, an initial matrix (FIG. 8(*a*)) is reorganized into compacted co-clusters (FIG. 8(*b*)), following the steps discussed in the previous section.

Second, the 'white-spots' of FIG. 8(*b*) are extracted, the 'white-spots' become the 'black-spots' of FIG. 8(*c*), after color inversion; these 'black-spots' are as many potential recommendations.

These recommendations can further be ranked from stronger to weaker, based on existing information available about the cores/data.

First, how to accomplish the reorganization of the adjacency matrix is explained in details. As discussed earlier, a two-step approach is used: an initial fast phase 'coarsens' the matrix and extracts basic co-cluster pieces (block S20 in FIGS. 3-4). A second phase iteratively refines the discovered co-clusters by progressively merging them (block S30 in FIGS. 3-4).

2.2 Co-Clustering Algorithm

An idea for making present algorithms scalable was to first reduce the size of the problem and then progressively improve the solution. One possibility is to commence with a K-Means-based approach to discover small, rudimentary co-clusters. This is continued with a more expensive refinement phase, as illustrated in FIGS. 3-4.

Algorithm: Assume a binary N×M input matrix $X \in \{0, 1\}^N \times \{0, 1\}^M$. To extract elementary co-cluster structures, clustering is performed separately on rows and columns. Row clustering treats each object as a [1×M] vector. Similarly, column clustering considers each object as a [1×N] vector derived by transposing each column. Clusters found on rows and columns are combined to form the initial co-clusters.

The decision to perform clustering separately on each dimension is not arbitrary. Rather, Inventors have realized from recent works that performing a K-Means type clustering separately on each dimension may provide constant factor approximations to the best co-clustering solution under a K-Means-driven optimization function. Such optimization functions are for instance discussed in A. Anagnostopoulos, et al., "Approximation Algorithms for Co-clustering". Therefore, an outcome of a co-clustering process may reside within rigid quality bounds from the optimal solution. Having realized that, it makes sense to contemplate a subsequent refinement, aiming at obtaining more meaningful clusters.

Also, contrary to most existing solutions, present approaches do not require an explicit setting of the parameter K, the number of co-clusters (or more precisely K clusters in one dimension and L clusters in the second dimension). Instead, present methods seed an initial number of co-clusters using a K-Means algorithm. An additional reorganization process driven by additional compacting steps S30 leads the search toward a very good compromise regarding the final number of co-clusters. The algorithm commences with a value of K that is not large enough, so as to lead to a less cluttered display. Typically, a value of K=10 can be used, just as done in the experiments reported in FIGS. 6-7. The second stage progressively decides how the basic co-clusters will be reshuffled and merged. To select the initial seeds for clustering, the K-Means++ variant is desirable, which exhibits provable guarantees with respect to the optimal solution and has been known to provide stable results.

Therefore, at the end of the execution of the double K-Means clustering, we end up with a K×K block matrix. Next, a process of moving blocks of rows or blocks of columns is initiated, such that the rearrangement results in a more uniform matrix. To evaluate the uniformity of the resulting matrix we adapt an information theoretic criterion.

Entropy measure. Consider a set of positive real numbers $P=\{p_1, p_2, \ldots, p_n\}$ such that $$\sum_{i=1,n} p_i = 1$$

(probability mass function). Entropy can be defined as:

$$E(P) = -\sum_{i=1,n} p_i \log p_i. \quad \text{(Eq. 10)}$$

Because $E(P) \in [0 \ldots \log n]$ for every n, we may compare entropy values of different-sized sets by suitably normalizing, e.g., $$E_n(P)=E(P)/\log n \in [0 \ldots 1]. \quad \text{(Eq. 11)}$$

Entropy, in particular as defined above, measures how uneven a distribution is. In present settings it assesses the distribution of nonempty cells of the matrix (black spots) in the discovered co-clusters. Consider the set of K×K blocks in the resulting matrix from the double K-Means clustering. For every block i, having size $n_i$ (overall number of cells in block i); the number of nonempty cells (ones) within it as $$ones_i = \sum_{k,l} e_{kl}^{(i)}. \quad \text{(Eq. 12)}$$

The density of block i can then be defined as $\rho_i = ones_i/n_i$. If we normalize all the densities, i.e., divide all $\rho_i$'s by $$\rho_{sum} = \sum_{i=1,K} \rho_i \quad \text{(Eq. 13)}$$

we can compute the entropy of the set of normalized densities:

$$p_i = \frac{\rho_i}{\rho_{sum}}. \quad \text{(Eq. 14)}$$

This measure captures the concept of descriptive co-clusters and uniform matrix since it promotes blocks of similar densities.

For example, for a 3×3 block matrix, a distribution of 2 dense blocks and 7 sparse blocks would be desirable (lower entropy) to a distribution of 4 dense blocks and 5 sparse blocks, a thing that promotes the merging of similar rows or columns.

The initial double K-Means process serves as a seeding step for the subsequent refinement phase. The resulting K×K block matrix is progressively merged, with the purpose of leading to a more concise representation of the data co-clusters. At every step, a candidate pair of either rows or columns (whichever is most similar) is selected and merged, as discussed in details in the previous section.

To assess the similarity between two blocks of rows (columns), each evaluated block can for instance be treated as a vector $v=(\rho_1, \rho_2, \ldots, \rho_K)$ with entries equal to the densities of the corresponding blocks (co-clusters). The distance between two block rows (or block columns) is e.g., the $L_2$-Norm of the corresponding densities:

$$D(v_k, v_l) = \sqrt{\sum_{i=1,K} \left(\rho_i^{(k)} - \rho_i^{(l)}\right)^2} \bigg/ K. \quad \text{(Eq. 15)}$$

Figures 5A, 5B, 5C, 5D:
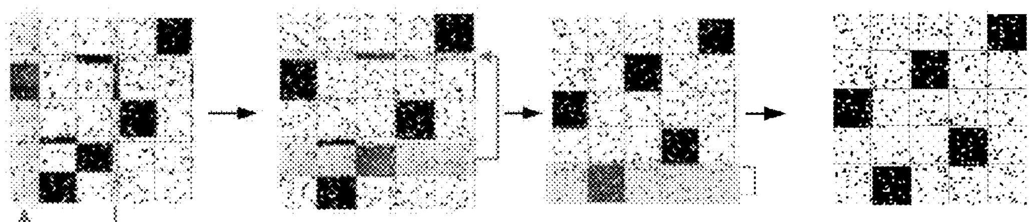
FIGS. 5A, 5B, 5C and 5D illustrate, graphically, successive operations of (i) determinations of most similar parallel block sequences (either two rows or columns of blocks), and (ii) subsequent merging of the determined sequences into single block sequences, for an example of input matrix.

The vectors are normalized by their length, because in the process of merging we might end up with different number of rows or column blocks. Therefore it is necessary to compensate for this discrepancy. FIGS. 5A-5D shows three iterations of the merging process. In FIG. 5A, columns 4 and 1 are merged because they were more similar than any of the candidate columns. However, at FIG. 5B, columns 6 and 2 are chosen for merging, etc.

How beneficial is this merging is evaluated by comparing the entropy of the block matrix before and after merging, as otherwise illustrated in FIG. 3. In order to avoid the unnecessary influence of the unchanged columns or rows, the entropy is only computed for the two block rows or columns that are merged. This process continues while the value of the entropy decreases. The process terminates when a candidate merge finally leads to larger entropy after the merging rather than beforehand. An example is shown in FIG. 5D: additional merging of any two columns or rows would result in an increase of the entropy in that case.

We have now described all components of the co-clustering algorithm: the seeding component based on K-Means primitive on each of the dimension, and the final merging steps until a relevant number of co-clusters is determined using an entropy-based stopping criterion. A running example of algorithm is given in FIGS. 6-7, discussed earlier, and an example of pseudocode is given below.

---

Algorithm: Double K-Means with entropy-based co-cluster merging
00: procedure CoCluster(X) {X: an m × n binary matrix}
01: $R = \{r_1, r_2, \ldots, r_K\}$ ←K-means++(set of rows of X)
02: $C = \{c_1, c_2, \ldots, c_k\}$ ← K-means++(set of columns of X)
03: entropyDiff ← 0
04: while entropyDiff < 0 do
05: $\{r_i, r_j\} \subset R$ ← two most similar elements of R ($i \neq j$)
06: $\{c_g, c_h\} \subset C$ ← two most similar elements of C ($g \neq h$)
07: if $dist(r_i, r_j) < dist(c_g, c_h)$ then
08: {Attempt to merge block rows $r_i$ and $r_j$}
09: entropyDiff← MERGE($r_i$, $r_j$)
10: else
11: {Attempt to merge block columns $c_g$ and $c_h$}
12: entropyDiff ← MERGE($c_g$, $c_h$)
13: end if
14: end while
15: end procedure
Output: A partition of the row set and the column set into $(r_1, r_2, \ldots, r_r)$ and $(c_1, c_2, \ldots, c_c)$ (with $r, c \leq K$), respectively.
16: function MERGE($T_1$, $T_2$)
17: {$T_1$, $T_2$: block rows or columns to be merged}
18: entropyPre ← entropy({$T_1$, $T_2$}) {initial entropy computed for {$T_1$, $T_2$} as before merging }
19: $T_1 \leftarrow T_1 \cup T_2$
20: entropyPost ← entropy({$T_1$})
21: entropyDiff ← entropyPost − entropyPre
22: if entropyDiff < 0 then
23: update the sets of block rows and columns R, C
24: end if
25: return entropyDiff
26: end function
Output: Difference between entropy values after merging block rows or columns ($T_1$, $T_2$) and before it.

---

Complexity: The above algorithm consists of two parts. First, rows and columns of the input matrix are clustered with the K-Means++ algorithm which results in a K×K block matrix. This has linear complexity to the number of objects. The second part iteratively merges blocks of rows or blocks of columns. At every step one pair of block rows is merged as long as the entropy measure decreases.

Thus there can be at most 2 K iterations. At every iteration the pair of most similar block columns and rows is computed which required at most $O(|C||R|^2)$ $(O(|R||C|^2))$ time for R (=|R|) rows and C (=|C|) columns. As one of R and C decreases by 1 for every iteration, the total cost over all iterations is at most $O(K^4)$. The pessimistic cost of computing entropy at every iteration is O(nm) (considering an m×n input binary matrix), however its average cost is O(nm/K) as only the entropy of the block rows or columns that are about to be merged is computed. The overall time complexity of the algorithm is therefore $O(nmK+K^4)$. Note that K is the number of initial clusters in rows and columns, which is constant and usually small (in most settings used so far, typically K=10), hence in practice our algorithm exhibits linear runtime complexity of O(nm).

Recommendations: The previous process reveals compacted co-clusters not visible in the original (unordered) adjacency matrix. For real data, the co-clusters will not be fully uniform but are expected to contain 'white-spots' (in the sense of FIG. 8(*b*)). These 'white-spots' represent statistical exceptions or abnormalities, e.g., they relate to nodes that exhibit similar data acquisition patterns as a number of other nodes, but which have not yet accessed some particular data, compared to other nodes within a same co-cluster. Thus, the 'white-spots' corresponds to potential recommendations/actions. To summarize, what is exploited here is the existence of globally-observable patterns for making individual recommendations/actions.

Finally, not all 'white-spots' may be equally important. Thus, they may possibly be further ranked according to additional metadata attached to the entities.

2.3 Results

Performance: First, the runtime of the algorithm of §2.1.1 is evaluated in comparison to spectral and hierarchical clustering approaches. Not only it is shown that embodiments of the present invention are dramatically more expedient, but also they results in better quality co-clusters. All experiments reported hereafter have been executed on a Mac Mini 2 Ghz system; the co-clustering code was written in Java.

The runtime of the present approach is evaluated against the spectral based technique of Dhillon, "Co-clustering Documents and Words using Bipartite Spectral Graph Partitioning,", which relegates the problem into a min-cut of a graph. For the experiment, data were created by inserting artificial co-cluster structures and reshuffling the array. The average density ρ of the matrices was ρ=5%; therefore 95% of the values were zeros. This was chosen to simulate approximately typical densities as encountered with real data. The results are summarized in FIG. 9, which compare runtime performances of an embodiment of the invention vs. a spectral co-clustering approach of Dhillon, "Co-clustering Documents and Words using Bipartite Spectral Graph Partitioning". The vertical axis represent time (in seconds), the horizontal axis represents the number (in thousands) of rows involved. The runtime of an agglomerative hierarchical co-clustering approach was also evaluated (not shown). However, this latter approach poses severe scalability issues. In a matrix with more than 2000 objects the runtime exceeds 50 sec. The spectral-based approach exhibits larger runtimes than our methodology. Our approach which exhibits very low-latency and linear scalability to the number of data objects. Notably, the response time is consistently lower than 7 sec for all experiments up to 90K objects.

Co-Cluster Detection: The present approach is robust even in the presence of noise. Given a reference block-diagonal matrix (FIG. 10.A(a) or FIG. 10.B(a)), before it is reshuffled (FIG. 10.A(b) or FIG. 10.B(b)), "salt-and-pepper" noise was introduced. This was done in an effort to dilute the strength of the original patterns. We compare the outcomes of the present approach (FIG. 10.A(c) or FIG. 10.B(c)) to the previous spectral-based approach's (FIG. 10.A(d) or FIG. 10.B(d)). The results are compared in FIGS. 10.A and 10.B, which consider, FIG. 10.A: a 5×5 block matrix with moderate noise; FIG. 10.B: a 8×8 block matrix with significant noise density of 50%. In each of FIGS. 10.A and 10.B, The present algorithm can detect accurately the original patterns, even in the presence of excessive noise. In addition, the present algorithm automatically detects the number of final co-clusters. In contrast, for the spectral-based approach the correct number K of co-clusters has to be explicitly provided. In both the cases of FIG. 10.A or 10.B, the spectral-based method returns results of lower quality. Note that the order of co-clusters obtained is different than on the original matrix. This is not important, at least not for most applications contemplated herein. Still, the output could be standardized to the original block-diagonal, by an appropriate reordering of the co-cluster outcome.

Graphical Interface: A simple prototype interface was built (not shown) to showcase the developed technology. The interface has been developed in Adobe Flex, while the algorithms and corresponding data services were implemented in Java/JSP. This prototypal GUI consists of three panes: a) a left pane showing categorizations of entities. The discovered clusters are displayed below. b) The middle pane is the co-clustered matrix and the intensity of each co-cluster box corresponds to the density of the discovered co-clusters. c) The right pane offers three accordion views: the entities/entities (e.g., nodes/data) contained in the selected co-cluster; statistics on the selected co-cluster; and potential recommendations contained in it.

To conclude, approaches have been presented, which exhibit linear-complexity co-clustering algorithms. These approaches first searches for rudimentary co-clusters structures and then combine them into a better, more compact, solution. Most embodiments are parameterless and are directly applicable on large scale data matrices even without parallelization.

While the present invention has been described with reference to a limited number of embodiments, variants and the accompanying drawings, it will be understood by those skilled in the art that various changes may be made and equivalents may be substituted without departing from the scope of the present invention. In particular, a feature (device-like or method-like) recited in a given embodiment, variant or shown in a drawing may be combined with or replace another feature in another embodiment, variant or drawing, without departing from the scope of the present invention. Various combinations of the features described in respect of any of the above embodiments or variants may accordingly be contemplated, that remain within the scope of the appended claims. In addition, many minor modifications may be made to adapt a particular situation or material to the teachings of the present invention without departing from its scope. Therefore, it is intended that the present invention not be limited to the particular embodiments disclosed, but that the present invention will include all embodiments falling within the scope of the appended claims. In addition, many other variants than explicitly touched above can be contemplated. For example, methods as disclosed herein can be contemplated to represent accessing patterns between sets of cores and sets of data.

The invention claimed is:

1. A computer-implemented method for identifying relationships between entities, the method comprising:

accessing a first data structure being a two-dimensional array of scalar elements (e, $e_{ij}$, $e_{kl}^{(i)}$ representable as a matrix, each of the scalar elements capturing a relationship between two entities;

reorganizing the first data structure by clustering the scalar elements separately on each dimension of the two-dimensional array, to obtain a second data structure, representable as a K×M block matrix, which is an arrangement of rows and columns of blocks, wherein each block is a reordered sequence of rows and/or columns of the first data structure;

compacting the second data structure by:

determining two parallel block sequences, which are the most similar according to a given distance measure, the parallel block sequences being either distinct rows or distinct columns of blocks of the second data structure; and reorganizing the second data structure by merging the two determined sequences into a single block sequence , wherein the $n^{th}$ block of the single sequence is the union of:

the $n^{th}$ block of a first one of the two parallel sequences; and the $n^{th}$ block of a second one of the two parallel sequences, wherein a compacted data structure is obtained which is representable as a K−1×M or a K×M−1 block matrix;

repeating the compacting, using a compacted data structure as input, in place of the second data structure; and identifying, in a graphical user interface, one or more blocks of a compacted data structure and/or selected scalar elements therein, wherein the graphical user interface is implemented by a processor that has a reduced runtime based on the compacted data structure.

2. The method of claim 1, wherein, at the compacting, the parallel block sequences determined are merged into a single block sequences if a final entropy of the single block sequence as after merging is reduced compared to an initial entropy of the parallel block sequences before merging, each of the initial entropy and the final entropy normalized according to the respective numbers of blocks involved.

3. The method of claim 2, wherein, at the compacting, each of the initial and final entropies is computed according to normalized intra-block densities, an intra-block density of a given block being computed based on an average value of the scalar elements in the given block.

4. The method of claim 3, wherein, at the compacting: the final entropy computed is proportional to $$\frac{-\sum_{i=1,K} p_i \log p_i}{\log K};$$

where i runs over each block within a sequence containing K blocks, and $p_i$ is the $i^{th}$ of the normalized intra-block densities.

5. The method of claim 4, wherein, at the compacting: the initial entropy of the parallel block sequences is proportional to $$\frac{-\sum_{i=1,2K} p_i \log p_i}{\log 2K};$$

where i runs over each block of the two parallel block sequences, containing 2K blocks in total.

6. The method of claim 1, wherein identifying the two parallel block sequences comprises computing distances between blocks of the parallel block sequences, based on intra-block densities, and distances between parallel block sequences are computed as an $L_2$-Norm of the intra-block densities.

7. The method of claim 1, wherein the first data structure accessed is a two-dimensional array of scalar elements, which captures relationships between at least $10^4$ entities.

8. The method of claim 1, wherein the first data structure accessed comprises scalar elements being binary or real-number values.

9. The method of claim 1, wherein the first data structure accessed is representable as an adjacency matrix of a bipartite graph, a bipartite graph of entities versus entity attributes.

10. The method of claim 1, wherein the reorganizing uses a K-means ++algorithm.

11. A computer-implemented method for identifying an abnormal relationship between two entities, comprising the method according to claim 1, and wherein the identifying comprises:

identifying a given scalar element in a given block of a compacted data structure, which has a value departing from an average value of the scalar elements of the given block as well as the two entities linked by the relationship captured by the given scalar element.

12. A method of resolving an abnormal relationship between two entities, comprising the method according to claim 11, and further comprising:

changing a real-world relationship, linking two real-world entities, and corresponding to the relationship captured by the given scalar element, such that the real-world relationship corresponds to a value not anymore departing from the average value of the scalar elements of the given block.

13. A method according to claim 1, wherein identifying comprises:

displaying a graphical representation of one or more dense blocks of a compacted data structure, and emphasizing the one or more dense blocks to a user.

14. A method according to claim 1, wherein identifying comprises:

emphasizing one or more scalar elements of one or more dense blocks of a compacted data structure, which one or more scalar elements have values departing from average values of scalar elements of the one or more dense blocks, by displaying a negative of the one or more dense blocks.

15. A computer program product comprising a non-transitory computer-readable storage medium having computer-readable program code embodied therewith, the computer-readable program code configured to implement the method to:

accessing a first data structure being a two-dimensional array of scalar elements ($e$, $e_{ij}$, $e_{kl}^{(i)}$ representable as a matrix, each of the scalar elements capturing a relationship between two entities;

reorganizing the first data structure by clustering the scalar elements separately on each dimension of the two-dimensional array, to obtain a second data structure, representable as a K×M block matrix, which is an arrangement of rows and columns of blocks, wherein each block is a reordered sequence of rows and/or columns of the first data structure;

compacting the second data structure by:

determining two parallel block sequences, which are the most similar according to a given distance measure, the parallel block sequences being either distinct rows or distinct columns of blocks of the second data structure; and reorganizing the second data structure by merging the two determined sequences into a single block sequence , wherein the $n^{th}$ block of the single sequence is the union of:

the $n^{th}$ block of a first one of the two parallel sequences; and the $n^{th}$ block of a second one of the two parallel sequences, wherein a compacted data structure is obtained which is representable as a K−1×M or a K×M−1 block matrix;

repeating the compacting, using a compacted data structure as input, in place of the second data structure; and identifying, in a graphical user interface, one or more blocks of a compacted data structure and/or selected scalar elements therein, wherein the graphical user interface is implemented by a processor that has a reduced runtime based on the compacted data structure.

* * * * *